United States Patent [19]

MacManus et al.

[11] Patent Number: 5,097,043

[45] Date of Patent: * Mar. 17, 1992

[54] PROCESS OF PREPARING CAPTOPRIL

[75] Inventors: Patrick A. MacManus, Dublin; Peter Walsh, County Dublin, both of Ireland; Adrian J. Kilbane, Rambouille, France

[73] Assignee: E. R. Squibb & Sons, Inc., Princeton, N.J.

[*] Notice: The portion of the term of this patent subsequent to Mar. 19, 2008 has been disclaimed.

[21] Appl. No.: 609,310

[22] Filed: Nov. 5, 1990

Related U.S. Application Data

[63] Continuation of Ser. No. 144,159, Jan. 15, 1988, Pat. No. 5,001,251.

[51] Int. Cl.$^5$ ............................................. C07D 207/16
[52] U.S. Cl. ...................................... 548/533; 562/401
[58] Field of Search ......................... 548/533; 562/401

[56] References Cited

U.S. PATENT DOCUMENTS 4,346,045 8/1982 De Heij ........................... 562/401 X
4,585,595 4/1986 Houbiers ............................ 558/255
5,001,251 3/1991 MacManus ........................... 558/255

Primary Examiner—Richard L. Raymond
Attorney, Agent, or Firm—Burton Rodney

[57] ABSTRACT

An optically active amine compound and a method for preparing same are provided which compound has the structure

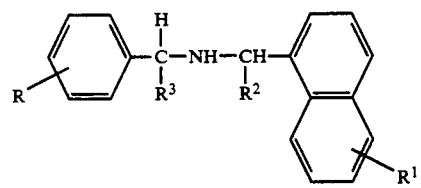

in the form of its R-(+) enantiomer or S-(−) enantiomer, wherein R and $R^1$ are independently H, lower alkyl or halogen, $R^2$ is H or lower alkyl and $R^3$ is lower alkyl, the optically active amine is useful in the optical resolution of DL-3-acylthio-2-methylpropanoic acid wherein acyl is acetyl or benzoyl. The optically active D-(+)-3-acylthio-2-methylpropanoic acids are used as intermediates for preparing antihypertensive agents, such as captopril.

4 Claims, No Drawings

PROCESS OF PREPARING CAPTOPRIL

This is a continuation of application Ser. No. 144,159, filed Jan. 15, 1988, now U.S. Pat. No. 5,001,251.

FIELD OF THE INVENTION

The present invention relates to an optically active amine which is useful in resolving DL-3-acylthio-2-methylpropanoic acid, and to methods for preparing such amine and for employing same in resolving such acid.

BACKGROUND OF THE INVENTION

The angiotensin converting enzyme inhibitor captopril, which has remarkable antihypertensive activity and has the structure

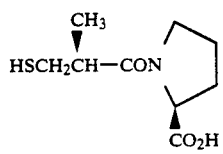

may be prepared by reacting the resolved D-(−)-3-acetylthio-2-propanoic acid with thionyl chloride to form its acid chloride, reacting the acid chloride with L-proline in the presence of base and then deacylating the resulting proline derivative to give captopril.

The starting D-(−)-3-acetylthio-2-propanoic acid may be obtained by resolution of DL-3-acylthio-2-methylpropanoic acid employing an optically active amine. For example, Ohashi U.S. Pat. No. 4,297,282 (assigned to Sumitomo Chemical Company) discloses a process for the optical resolution of DL-α-methyl-β-acylthio-propionic acids to ultimately obtain D-α-methyl-β-acylthiopropionic acid (useful in preparing captopril) wherein the resolving agent employed is an optically active amine of the formula

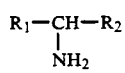

wherein $R_1$ is methyl and $R_2$ is α-naphthyl or $R_1$ is

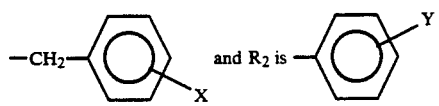

wherein X and Y are each halogen, methyl or halogen. Thus, such optically active amines include

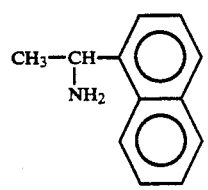

or

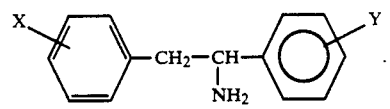

Ohashi U.S. Pat. No. 4,325,886 (assigned to Sumitomo Chemical Company) is similar in disclosure to U.S. Pat. No. 4,297,282 except that the optically active amine employed has the formula

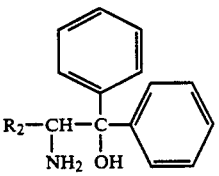

wherein $R_2$ is methyl, isopropyl or isobutyl.

DeHeij U.S. Pat. No. 4,346,045 (assigned to Oc-Andeno B.V.) discloses a process for resolving DL-S-benzoyl-β-mercaptoisobutyric acid using D-(+)-N-benzyl-α-phenethylamine (NBPA), that is,

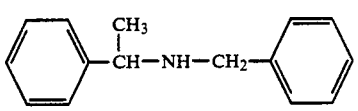

DESCRIPTION OF THE INVENTION

In accordance with the present invention, an optically active amine is provided which is useful in optically resolving DL-3-acylthio-2-methylpropanoic acid, which amine has the structure

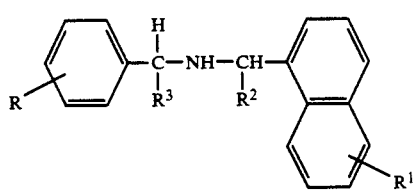

I.

and includes the R-(+) enantiomer and the S-(−)enantiomer, wherein R and $R^1$ may be the same or different but are independently selected from H, glower alkyl or halogen, $R^2$ is H or lower alkyl, and $R^3$ is lower alkyl.

The term "lower alkyl" or "alkyl" as used herein refers to straight and branched chain radicals of up to 12 carbons and preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, including the various branched chain isomers thereof.

The term "halogen" or "halo" as used herein refers to chlorine, bromine, fluorine or iodine with chlorine being preferred.

Preferred optically active amines of formula I are the R-(+) enantiomer where R, $R^1$ and $R^2$ are each H. Most preferred is the R-(+) enantiomer of the compound IA

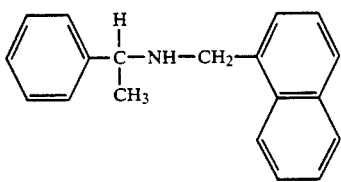

IA

In addition, in accordance with the present invention, a method is provided for preparing the optically active amines of formula I which includes the steps of forming a solution of a compound of the structure

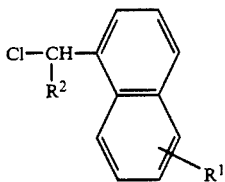

II in an organic solvent such as toluene, ethyl acetate, chloroform or methylisobutyl ketone and an organic base such as triethylamine, tripropyl amine or tributylamine, treating the solution with an amine of the structure

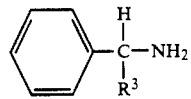

III employing a molar ratio of II:III of within the range of from about 1.05:1 to about 1.2:1, heating the mixture to a temperature within the range of from about 70 to about 120° C., under an inert atmosphere, such as nitrogen, to form the compound of formula I and recovering such compound from the reaction mixture.

Further, in accordance with the present invention, a process is provided for the optical resolution of DL-3-acylthio-2-methylpropanoic acids which includes the steps of contacting a DL-3-acylthio-2-methylpropanoic acid of the structure IV

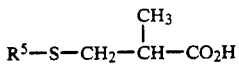

IV wherein $R^5$ is acetyl or benzoyl (which may or may not be substituted with lower alkyl or halogen) with an optically active amine of formula I in the presence of an organic solvent such as isopropyl alcohol, sec-butanol or isobutyl acetate employing a molar ratio of acid IV to amine I of within the range of from about 1.05:1 to about 1:1, while heating the reaction mixture to a temperature within the range of from about 15° C. to about 40° C., to form diastereoisomeric salts, subjecting the so-formed diastereoisomeric salts to fractional crystallization to separate the D-acid salt from the L-acid salt, and then treating the individual diastereoisomeric salt with acid, such as hydrochloric acid, sulphuric acid or perchloric acid employing a molar ratio of salt to acid of within the range of from about 0.5:1 to about 2.0:1, to form D-(−)-3-acylthio-2-methylpropanoic acid and L-(−)-3-acylthio-2-methylpropanoic acid.

The individual diastereomeric salt may also be converted to the free acid by first partitioning between an organic solvent such as dichloromethane or toluene and an aqueous base such as aqueous sodium hydroxide or sodium carbonate, separating the aqueous layer, acidifying with aqueous acid and extracting the recovered acid into an organic solvent such as dichloromethane or toluene.

The recovered D-(−)-3-acylthio-2-methyl-propanoic acid may then be employed as a starting material to prepare captopril (formula IV where $R^5$ is acetyl) or

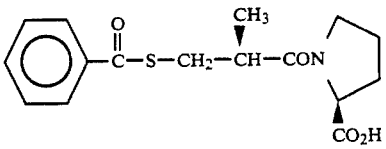

which also has antihypertensive properties.

The following Examples represent preferred embodiments of the invention. Unless otherwise indicated, all temperatures are expressed in degrees Centigrade.

EXAMPLE 1

Preparation of
R-(+)-N-(1-Naphthylmethyl)-α-methylbenzylamine
[R(+)-amine]

1-Chloromethylnaphthalene (154 g, 1.05 equivalents) was dissolved in toluene (400 ml) with triethylamine (130 ml) and purged with nitrogen for 10 minutes.

R-(+)-α-methylbenzylamine (100 g) was added and the solution heated at 70°–75° C. under nitrogen for 20 hours during which time a precipitate of triethylamine hydrochloride formed. The mixture was cooled to ambient and washed with water (200 ml) to remove triethylamine hydrochloride. The toluene was evaporated, the residue dissolved in methylene chloride (600 ml) and water (200 ml) added. Concentrated hydrochloric acid (150 ml) was added over 20 minutes to form amine hydrochloride precipitate. The precipitate was filtered and washed with water (400 ml). The solid was slurried in methylene chloride (500 ml), filtered and washed with methylene chloride (100 ml). The amine was isolated by basifying the salt to pH 13.0, separating the methylene chloride layer, drying over sodium sulphate and evaporating to dryness. Weight of amine was 122 g, 56.5%. $a_D^{ethanol} = +34°$.

The structure was confirmed by $^1H$ and $^{13}C$ NMR and microanalysis of the hydrochloride salt. $C_{19}H_{20}NCl$ found (theory): C, 76.90 (76.63); H, 7.00 (6.72); N, 4.62 (4.70); Cl, 11.83 (11.93) %.

EXAMPLE 2

Resolution of DL-3-Acetylthio-2-methylpropanoic Acid with R-(+)-N-(1-Naphthylmethyl)-α-methyl Benzylamine DL-3-Acetylthio-2-methylpropanoic acid (32.56 g, 0.20 mole) and R-(+)-N-(1-naphthyl-methyl)-α-methylbenzylamine (50 g, 0.19 mole, 0.95 equivalent) were dissolved in isopropyl alcohol (270 ml) by warming to about 40° C. A clear solution was obtained which was cooled to 30° C., seeded and the temperature allowed to drift to ambient (18° C.). During 2 hours a crop of fluffy crystals formed. The mixture was left overnight in a refrigerator at 0°–2° C., without agitation. The crystals were filtered and washed with cold (0°-2° C.) isopropyl alcohol (25 ml), and dried at 55° C. under vacuum to yield 27.6 g of crude salt.

The salt was recrystallized from isopropanol (110 ml) by warming to 45° C., cooling to 30° C., seeding and allowing the solution to drift to ambient temperature without stirring. A thick precipitate formed within 2 hours. The mixture was cooled in the refrigerator overnight, filtered, washed with cold isopropyl alcohol (20 ml), and dried under vacuum at 55° C. to yield 24 g of salt.

The salt was dissolved in methylene chloride (100 ml) and water (150 ml) added. The pH was adjusted to 10.5 by addition of 10 M NaOH with vigorous agitation. The layers were separated, and the aqueous layer was washed with methylene chloride (40 ml×2). The methylene chloride layer was retained for amine recovery.

Fresh methylene chloride (80 ml) was added to the aqueous phase which was then acidified to pH=1.5 with hydrochloric acid. The layers were separated and the aqueous layer washed with methylene chloride (40 ml×2). The combined methylene chloride was dried over sodium sulphate, filtered and evaporated to leave an oil.

Yield of (−) acid=9.1 g; $\alpha_D^{ethanol} = -44.5°$.
Optical purity 96.6%.

The amine was recovered as follows:

a) The methylene chloride phase above was concentrated to yield 15.1 g of amine.

b) The combined isopropyl alcohol mother liquors were concentrated to an oil which was dissolved in methylene chloride (120 ml). Water (150 ml) was added and the pH adjusted to 10.5 by addition of 10 M NaOH. The layers were separated and the aqueous layer washed with methylene chloride (40 ml×2). The combined methylene chloride was dried and evaporated to yield 31.5 g of amine.

Total recovery of amine was 46.6 g, 93%.

EXAMPLES 3 to 15

Following the procedure of Example 1, using appropriate reagents, the following additional optically active organic amines may be prepared.

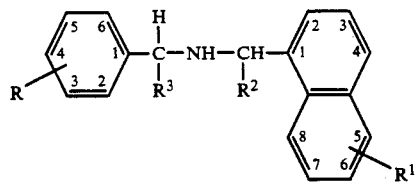

| Ex. No. | R(position) | $R^3$ | $R^2$ | $R^1$(position) |
|---|---|---|---|---|
| 3. | $CH_3(4)$ | $CH_3$ | H | H |
| 4. | Cl(4) | $C_2H_5$ | $CH_3$ | $CH_3(6)$ |
| 5. | H | $C_3H_7$ | H | $C_2H_5(5)$ |
| 6. | $C_2H_5(3)$ | $C_4H_9$ | $C_2H_5$ | H |
| 7. | Br(3) | $CH_3$ | H | $CH_3(5)$ |
| 8. | H | $C_2H_5$ | $C_3H_7$ | $CH_3(7)$ |
| 9. | $C_3H_7(4)$ | $C_3H_7$ | H | H |
| 10. | H | $C_4H_9$ | $C_4H_9$ | H |
| 11. | H | $CH_3$ | H | $CH_3(6)$ |
| 12. | Cl(3) | $C_2H_5$ | $C_5H_{11}$ | $CH_3(5)$ |
| 13. | $CH_3(4)$ | $C_3H_7$ | $CH_3$ | $CH_3(7)$ |
| 14. | H | $C_4H_9$ | H | H |
| 15. | H | $CH_3$ | H | $CH_3(6)$ |

EXAMPLE 16

S-(−)-N-(1-Naphthylmethyl)-α-methylbenzylamine

Following the procedure of Example 1 except substituting S-(−)-α-methylbenzylamine Following the procedure of Example 1 except substituting S-(−)-α-methylbenzylamine for R-(+)-α-methylbenzylamine for R-(+)-α-methylbenzylamine, the title compound is obtained.

EXAMPLE 17

Resolution of DL-3-Benzoylthio-2-methylpropanoic Acid with
R-(+)-N-(1-naphthylmethyl)-α-methylbenzylamine Following the procedure of Example 2 except substituting DL-3-benzoylthio-2-methylpropanoic acid for DL-3-acetylthio-2-methylpropanoic acid, resolution is accomplished.

EXAMPLE 18

Resolution of DL-3-Benzoylthio-2-methylpropanoic Acid with
S-(−)-N-(1-naphthylmethyl)-α-methylbenzylamine Following the procedure of Example 2, except substituting S-(−)-N-(1-naphthylmethyl)-α-methylbenzylamine for R-(+-N-(1-naphthylmethyl)-α-methylbenzylamine, the above benzoyl compound is resolved.

EXAMPLE 19

Resolution of DL-3-Acetylthio-2-methylpropanoic acid with
S-(−)-N-(1-naphthylmethyl)-α-methylbenzylamine Following the procedure of Example 2 except substituting S-(−)-N-(1-naphthylmethyl)-α-methylbenzylamine for R-(+)-N-(1-naphthylmethyl)-α-methylbenzylamine, the resolution is accomplished.

What is claimed is:

1. A process for preparing captopril, which comprises contacting DL-3-acetylthio-2-methylpropanoic acid of the structure

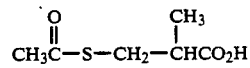

with an optically active amine of the formula

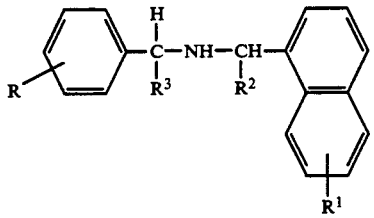

which is the R-(+) enantiomer of the S-(−) enantiomer, wherein R and $R^1$ are independently selected from H, lower alkyl or halogen, $R^2$ is H or lower alkyl and $R^3$ is lower alkyl, to form diastereoisomeric salts, subjecting the so-formed diastereoisomeric salts to fractional crystallization in a solvent to separate the D-acid salt from the L-acid salt, treating the individual diastereoisomeric salt with acid to form D-(−)-3-acetylthio-2-methylpropanoic acid and L-(−)-3-acetylthio-2- methylpropanoic acid, reacting the D-(−)-3-acetylthio-2-methylpropanoic acid with thionyl chloride to form the corresponding acid chloride, reacting the acid chloride with L-proline in the presence of base and then deacylating the resulting proline to give captopril.

2. The process as defined in claim 1 wherein R, $R^1$ and $R^2$ are each H and $R^3$ is $CH_3$.

3. The process as defined in claim 1 wherein the R-(+) enantiomer of the optically active amine is employed.

4. The process as defined in claim 1 wherein the optically active amine has the name R-(+)-N-(1-naphthylmethyl)-α-methylbenzylamine.

* * * * *